(12) United States Patent
Aman et al.

(10) Patent No.: US 12,295,717 B2
(45) Date of Patent: May 13, 2025

(54) INTRAVASCULAR SENSING DEVICES HAVING FLEXIBLE TIP STRUCTURE

(71) Applicant: TELEFLEX MEDICAL INCORPORATED, Morrisville, NC (US)

(72) Inventors: Michael Aman, Sinking Spring, PA (US); Jamie C. Rowe, Wernersville, PA (US); Igor Tentler, Collegeville, PA (US); Kurt Heinly, Wernersville, PA (US); Michael Harding, Reading, PA (US); Nick Horst, Leola, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 24 days.

(21) Appl. No.: 17/323,615

(22) Filed: May 18, 2021

(65) Prior Publication Data

US 2021/0275054 A1   Sep. 9, 2021

Related U.S. Application Data

(63) Continuation of application No. 15/442,024, filed on Feb. 24, 2017, now Pat. No. 11,006,854.

(51) Int. Cl.
| | |
|---|---|
| *A61B 5/00* | (2006.01) |
| *A61B 5/06* | (2006.01) |
| *A61B 5/283* | (2021.01) |
| *A61B 5/29* | (2021.01) |
| *A61B 8/00* | (2006.01) |

(Continued)

(52) U.S. Cl.
CPC .............. *A61B 5/065* (2013.01); *A61B 5/283* (2021.01); *A61B 5/29* (2021.01); *A61B 8/12* (2013.01); *A61B 8/445* (2013.01); *A61B 5/6852* (2013.01); *A61B 8/0841* (2013.01); *A61B 8/488* (2013.01)

(58) Field of Classification Search
CPC ....... A61B 5/065; A61B 5/283; A61B 5/6852; A61B 18/1492; A61B 2018/1497; A61B 5/042; A61B 5/0421; A61B 8/0841; A61B 8/12; A61B 8/488
See application file for complete search history.

(56) References Cited

U.S. PATENT DOCUMENTS

| | | | |
|---|---|---|---|
| 4,319,580 A | 3/1982 | Colley et al. | |
| 4,971,490 A | 11/1990 | Hawkins | |

(Continued)

FOREIGN PATENT DOCUMENTS

| | | | |
|---|---|---|---|
| CA | 2121353 A1 | 5/1993 | |
| CN | 1868409 A | 11/2006 | |

(Continued)

*Primary Examiner* — Eun Hwa Kim
(74) *Attorney, Agent, or Firm* — BakerHostetler

(57) ABSTRACT

An intravascular device, such as a stylet or catheter, having a flexible, atraumatic tip is disclosed. The intravascular device includes an elongate member having a proximal end, a distal end, and an inner lumen extending between the proximal end and the distal end; a ring electrode disposed at the distal end of the elongate member; an ultrasound sensor disposed at a distal end of the ring electrode; and a first electrical conductor configured to convey an electrocardiogram signal from the ring electrode to a processor. The first electrical conductor may comprise a tapered distal segment or a braided segment.

20 Claims, 9 Drawing Sheets

(51) Int. Cl.
*A61B 8/12* (2006.01)
*A61B 8/08* (2006.01)

(56) References Cited

U.S. PATENT DOCUMENTS

| | | | |
|---|---|---|---|
| 5,749,833 A | 5/1998 | Hakki et al. | |
| 5,954,649 A | 9/1999 | Chia et al. | |
| 6,134,463 A * | 10/2000 | Wittkampf | A61N 1/06 606/41 |
| 6,231,514 B1 | 5/2001 | Lowe et al. | |
| 6,241,726 B1 | 6/2001 | Chia et al. | |
| 6,306,106 B1 | 10/2001 | Boyle | |
| 6,662,055 B1 * | 12/2003 | Prutchi | A61N 1/056 607/122 |
| 7,479,141 B2 | 1/2009 | Kleen et al. | |
| 8,597,193 B2 | 12/2013 | Grunwald et al. | |
| 8,965,490 B2 | 2/2015 | Lee et al. | |
| 9,198,600 B2 | 12/2015 | Grunwald et al. | |
| 10,492,854 B2 | 12/2019 | Govari et al. | |
| 10,602,960 B2 | 3/2020 | Pameijer et al. | |
| 2002/0111548 A1 * | 8/2002 | Swanson | A61B 8/445 600/478 |
| 2004/0015065 A1 | 1/2004 | Panescu et al. | |
| 2006/0253032 A1 | 11/2006 | Altmann et al. | |
| 2007/0015996 A1 | 1/2007 | Camus et al. | |
| 2007/0129717 A1 | 6/2007 | Brown et al. | |
| 2009/0005675 A1 | 1/2009 | Grunwald et al. | |
| 2009/0287090 A1 | 11/2009 | Hadjicostis | |
| 2010/0222664 A1 | 9/2010 | Lemon et al. | |
| 2010/0249601 A1 | 9/2010 | Courtney | |
| 2014/0142670 A1 * | 5/2014 | Radhakrishnan | H01J 9/02 607/116 |
| 2015/0119674 A1 | 4/2015 | Fischell et al. | |
| 2015/0148877 A1 | 5/2015 | Thakkar et al. | |
| 2015/0173829 A1 * | 6/2015 | Lichtenstein | A61B 18/1492 606/34 |
| 2015/0342672 A1 | 12/2015 | Bencini et al. | |
| 2016/0278869 A1 | 9/2016 | Grunwald | |
| 2017/0202468 A1 * | 7/2017 | Nemec | A61M 25/0014 |

FOREIGN PATENT DOCUMENTS

| | | |
|---|---|---|
| CN | 1872000 A | 12/2006 |
| CN | 101208045 A | 6/2008 |
| EP | 1393674 A1 | 3/2004 |
| EP | 2213257 A2 | 8/2010 |
| EP | 2829222 A2 | 1/2015 |
| JP | 01172848 U | 12/1989 |
| JP | 07079980 A | 3/1995 |
| JP | 09503929 A | 4/1997 |
| JP | 09253063 A | 9/1997 |
| JP | 11-056854 A | 3/1999 |
| JP | 2005-152654 A | 6/2005 |
| JP | 2005-319313 A | 11/2005 |
| JP | 2009-142653 A | 7/2009 |
| JP | 2009-160397 A | 7/2009 |
| JP | 2010532227 A | 10/2010 |
| JP | 2015536201 A | 12/2015 |
| WO | 96/34561 A1 | 11/1996 |
| WO | 96/40344 A1 | 12/1996 |
| WO | 99/16347 A1 | 4/1999 |
| WO | 2005/072391 A2 | 8/2005 |
| WO | 2006/086152 A2 | 8/2006 |
| WO | 2007/005201 A1 | 1/2007 |
| WO | 2008/086615 A1 | 7/2008 |
| WO | 2012/040487 A1 | 3/2012 |
| WO | 2016/115208 A1 | 7/2016 |
| WO | 2016/168605 A1 | 10/2016 |

* cited by examiner

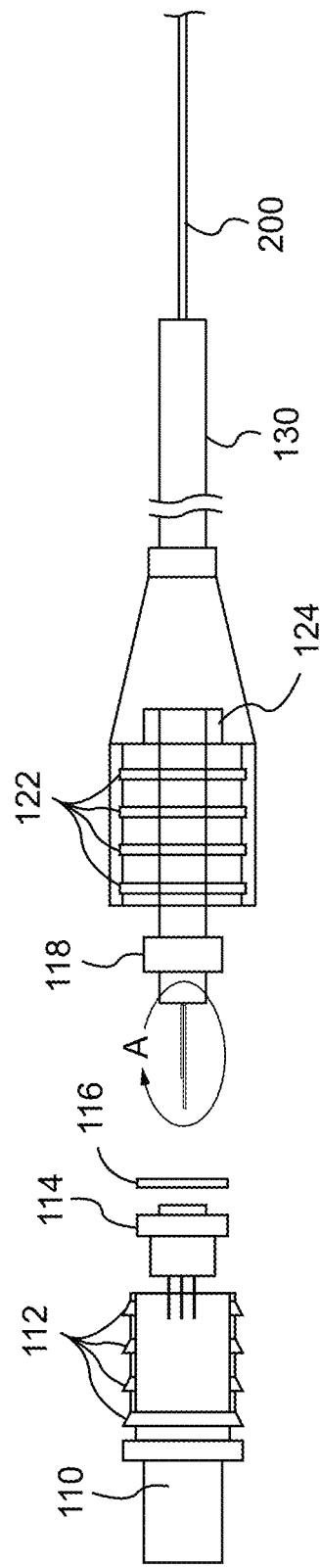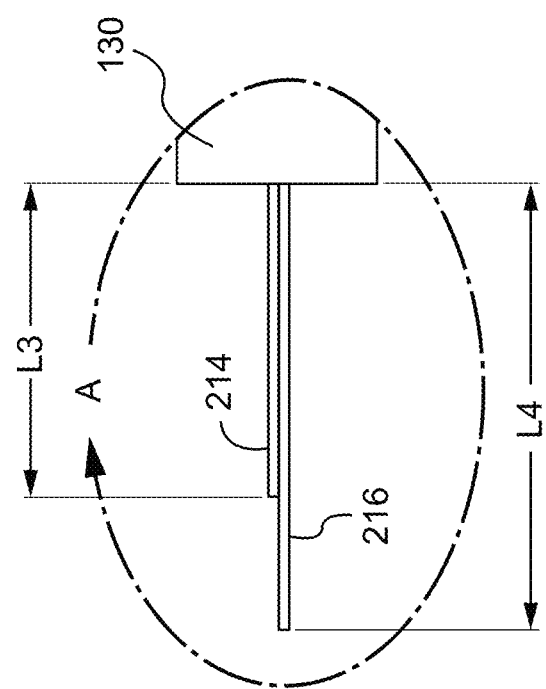
FIG. 2A
FIG. 2B

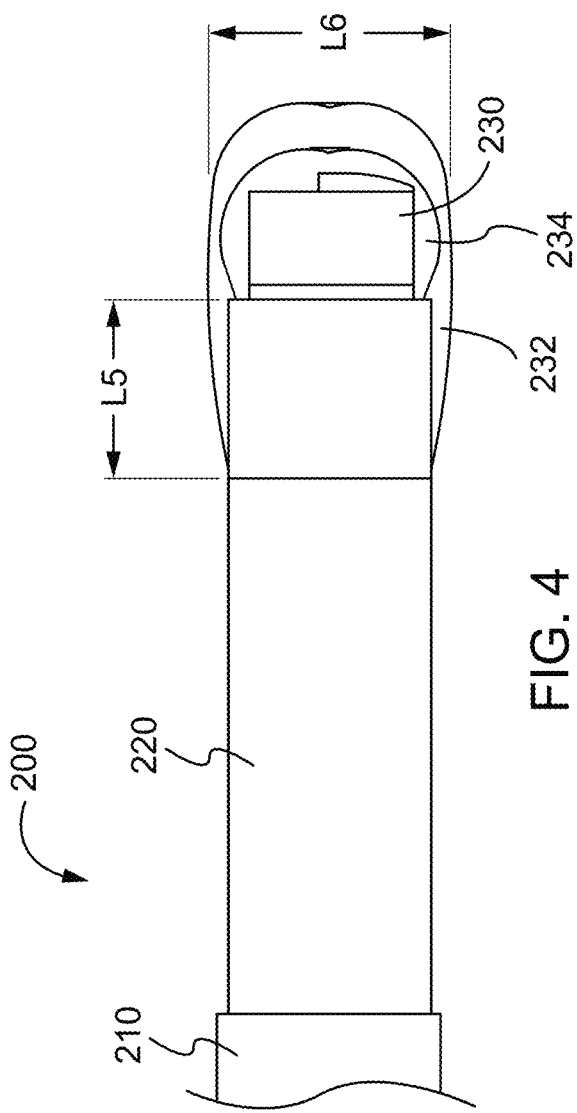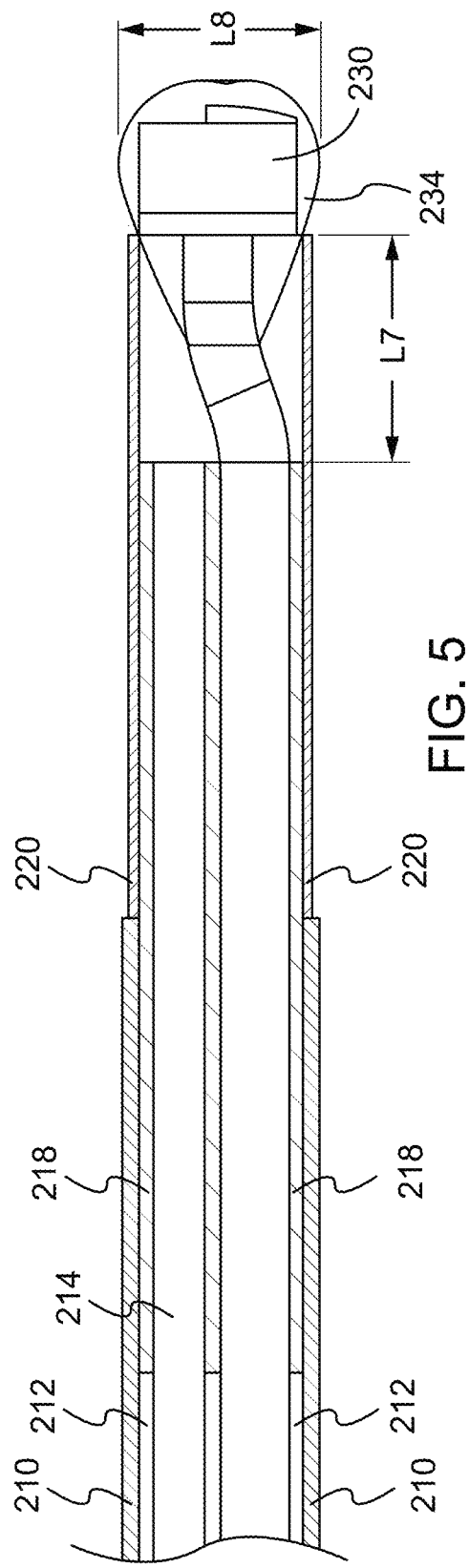

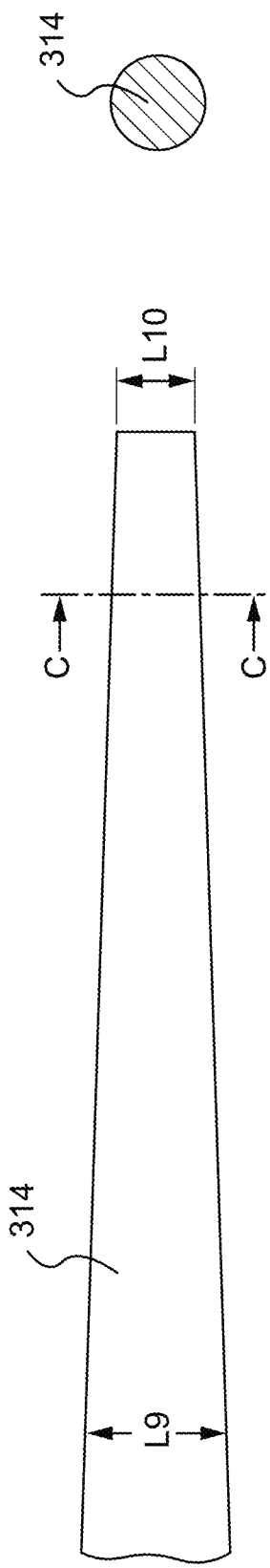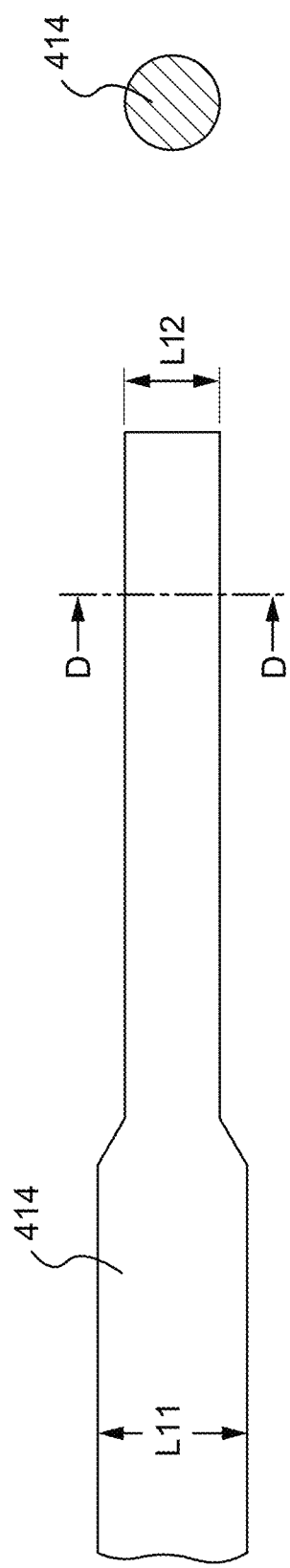

INTRAVASCULAR SENSING DEVICES HAVING FLEXIBLE TIP STRUCTURE

CROSS-REFERENCE TO RELATED APPLICATION

This application is a continuation of U.S. patent application Ser. No. 15/442,024 filed Feb. 24, 2017, which is expressly incorporated herein by reference in its entirety.

TECHNICAL FIELD

This disclosure generally relates to intravascular devices, such as stylets or catheters, and more specifically, a stylet having a flexible tip that includes one or more sensors.

BACKGROUND

Intravascular catheters, including peripherally inserted central catheters ("PICCs") may be used to administer nutritional agents, chemotherapy, antibiotics, or other medications to a patient, and meet other clinical needs such as hemodialysis and blood drawing. In general, it is necessary to place the tip of an intravascular catheter at a specific location within a patient, such as within the lower half of the superior vena cava to the cavoatrial junction. Traditionally, the tip location of an intravascular catheter is confirmed via X-ray imaging. But due to differences in patient anatomy and difficulties in navigating venous pathways, the process of placing an intravascular catheter within a patient is labor and time-intensive and may expose a patient to multiple rounds of X-ray imaging.

As an alternative to using X-rays, a stylet equipped with an electrocardiogram ("ECG") sensor (e.g., an ECG electrode) or a Doppler sensor (e.g., an ultrasonic transducer) may be used to confirm the tip location of an intravascular catheter as the catheter is being inserted through the venous pathway of a patient. The use of ECG signals or Doppler signals to track placement of catheters reduces the need for X-ray imaging, which reduces patient exposure to radiation and decreases the cost and time needed for placing catheters within patients.

Current sensor-equipped stylets may include stainless steel components. Oftentimes, the distal tips of these stylets are rigid in design, and therefore may damage vessel walls during catheter insertion. Therefore, there is a need for a stylet having a flexible tip such that injury to vessels is reduced.

SUMMARY

The foregoing needs are met, to a great extent, by an intravascular device, such as a stylet or catheter, having a flexible tip. In one or more aspects, the intravascular device includes an elongate member having a proximal end, a distal end, and an inner lumen extending between the proximal end and the distal end; a ring electrode disposed at the distal end of the elongate member; an ultrasound sensor disposed at a distal end of the ring electrode; a first electrical conductor configured to convey an electrocardiogram signal from the ring electrode to a processor; and an adaptor member connecting the first electrical conductor to the ring electrode. The first electrical conductor may comprise a tapered distal segment, where a distal portion of the tapered distal segment is attached to the adaptor member and a distal portion of the adaptor member is attached to the ring electrode. The proximal portion of the adaptor member can be disposed within the elongate member and the distal portion of the adaptor member can be disposed within the ring electrode.

In some aspects, the first electrical conductor may comprise a gradual taper that transitions from a larger diameter to a smaller diameter over 2 to 3 inches. In other aspects, the first electrical conductor may comprise a quick, steep taper that transitions from a larger diameter to a smaller diameter in a short distance, thereby providing a region of 2 to 3 inches at the smaller diameter. In still other aspects, the first electrical conductor may comprise multiple wires that end at different points, thereby creating greater flexibility in a region with fewer wires than a region with more wires. In yet another aspect, the first electrical conductor may comprise a variable-pitch braided wire reinforcement.

Details of one or more implementations of the disclosure are set forth in the accompanying drawings and the description below. Other aspects of the disclosure will be apparent from the description and drawings, and from the claims.

BRIEF DESCRIPTION OF THE DRAWINGS

In order that the disclosure may be readily understood, aspects of the disclosure are illustrated by way of examples in the accompanying drawings, in which like reference numerals refer to like elements throughout.

FIG. 2a is a partial cross-sectional view of a proximal end of an intravascular device including connectors and other structures for supporting a proximal end of a flexible tip stylet.

FIG. 2b is an enlarged view of electrical conductors or cables of a flexible tip stylet extending from a proximal end of a tubular member.

FIG. 4 is an enlarged view of an ECG electrode and an ultrasound sensor disposed at a distal end of a flexible tip stylet.

FIG. 5 is a cross-sectional view of an ECG electrode and an ultrasound sensor disposed at a distal end of a flexible tip stylet.

FIGS. 6a and 6b depict a first example of an electrical wire or conductor for conveying an ECG signal.

FIGS. 7a and 7b depict a second example of an electrical wire or conductor for conveying an ECG signal.

DETAILED DESCRIPTION

Figure 1:
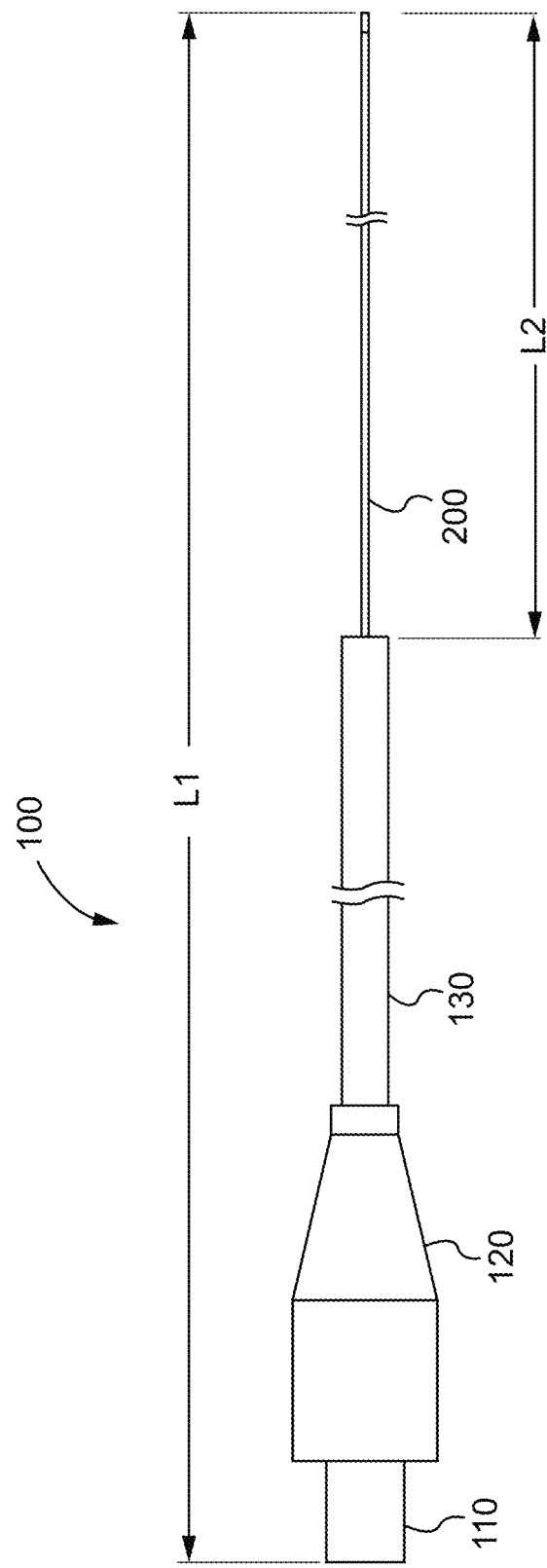
FIG. 1 is a side view of an intravascular device including a flexible tip stylet.

Access to a patient's vasculature is a known way to provide therapy, administer pharmacological agents and meet other clinical needs. Numerous procedures exist in both venous and arterial systems and are selected based on patient need. One challenge common to all vascular-based therapies is access to a specific location or section of a patient's vasculature. Another challenge of vascular-based access therapy is that X-ray imaging, and at times ultrasound imaging, is required in order to confirm the proper positioning and placement of intravascular devices, such as catheters, stylets, guidewires, and other elongate bodies, that are inserted percutaneously into the venous or arterial vasculature of a patient.

One common type of venue access procedure is central venous access. Central venous access involves the placement of a venous catheter in a vein that leads directly to the heart. Venous access devices are most often used for administering medications, such as antibiotics, chemotherapy drugs, and other intravenous drugs; administering fluids and nutritional compounds (e.g., hyperalimentation); transfusion of blood products; hemodialysis; and multiple blood draws for diagnostic testing; among others. Conventional central venous access devices are small, flexible tubes placed in large veins for people who require frequent access to their bloodstream. These devices often remain in place for long periods of time, such as a week, a month, or even longer.

Traditional surgically placed central catheters are increasingly being replaced by peripherally inserted central venous access devices such as PICCs. PICC lines usually cause fewer severe complications than central venous access devices and are used in a variety of clinical procedures, including long-term drug delivery, chemotherapy procedures, delivery of intravenous medications or intravenous nutrition, and blood draws. Insertion of PICC lines usually is a very time and labor-intensive procedure for hospital staff, which makes it expensive. During the procedure, the physician or nurse places the catheter into a superficial arm vein such as the cephalic, basilic, antecubital, median cubital, or other superficial vein with the goal of having the distal end of the catheter reach the superior vena cava. For example, after entering a superficial vein around an area where a patient's arm bends (e.g., the elbow), the catheter is advanced up the subclavian vein and the brachiocephalic vein before it enters the superior vena cava.

Methods of guiding PICC lines include external electromagnetic sensors and intravascular ECG-guided catheters. In the case of electromagnetic sensors, the PICC line is guided by assessing the distance between an electromagnetic element at the tip of the device, (e.g., a coil) and an external, out-of-body receiver. In the case of intravascular ECG-guided catheters, physicians rely on the classic increase in P-wave size to determine the location of catheter tips in the proximity of the sinoatrial node. Existing methods include using a catheter filled with saline with an ECG adaptor at the proximal end of the catheter that is connected to an ECG system.

In addition to guiding a catheter through the vasculature, the location of the catheter tip is very important to the success of a procedure. Catheters will generally function equally well for pressure measurement and fluid infusion if the tip is situated in any major vein, above or below the heart. It is also of major interest that the catheter tip stays in place after placement for the whole duration of the treatment. If the catheter tip moves, not only its effectiveness diminished but, in some situations, it can damage the heart or surrounding blood vessels. Typically, an interventional radiologist uses a fluoroscopic agent to delineate the veins in the body and subsequently verifies the correct positioning of the catheter tip by routinely taking post-operative X-rays.

Accordingly, there is a need for an apparatus that optimizes intravascular guidance and placement of catheters in a patient without the need to for a confirmatory X-ray. Removing the need for X-ray imaging reduces patient exposure to radiation and the cost and time associated with X-ray imaging. Further there remains a need for a catheter guidance and placement system that may be used to safely guide and place catheters in clinical environments other than in a radiology department. As such, there remains a need in the medical arts for instruments, systems and associated methods for locating, guiding and placing catheters and other instruments into the vasculature generally.

Systems and methods described herein provide an intravascular device that aids in the insertion and confirmation of the tip location of a catheter, such as a PICC. Such systems and methods use a flexible-tip, low impedance electrode to detect an intravascular ECG signal along with Doppler signals collected by a ultrasonic transducer to track the movement of a catheter through a patient's vasculature. By relying on ECG and Doppler data, systems and methods described herein negate the need for X-ray imaging, saving time and money and reducing radiation exposure. Such systems and methods employ low impedance ECG electrodes to ensure good quality ECG measurements. Such systems and methods also include a flexible tip design that reduces the potential of damaging a patient's vessel walls as a catheter is navigated through the patient's vasculature.

According to aspects of the disclosure, a stylet that may be positioned within a catheter includes an ECG electrode and an ultrasonic transducer. The ECG electrode may be electrically connected to an electrical conductor that transmits ECG signals from the ECG electrode to an external processor. The ultrasonic transducer may be mounted to a coaxial cable that transmits Doppler signals collected by the transducer to the external processor. A thermoset polymer tube may house both the electrical conductor of the ECG signals and the coaxial cable. The ECG signals and Doppler signals are transmitted over the length of the stylet via the electrical conductor and the coaxial cable, both of which may be soldered to a connector at a proximal end of the stylet. The connector may be configured to connect or plug into a console that interprets the signals and gives feedback to a user (e.g., physician, nurse) that is using the device to position a PICC in a patient's vasculature.

In some aspects, different components of an ECG and Doppler-equipped stylet may be constructed from materials including: (i) stainless steel, (ii) platinum iridium compounds, and (iii) silver epoxy. Stainless steel is a common used material in medical devices because of its biocompatibility, strength, and relatively low cost. Stainless steel is also a good conductor of electricity but has a high solution impedance, which makes it less effective at detecting electrical signals from a fluid. Platinum iridium compounds also conduct electricity well and have a low solution impedance, which makes them more ideal for detecting electrical signals from fluids. Because platinum is a soft material, iridium is added to increase the overall strength of the compound. Platinum iridium compounds, however, are generally softer and more expensive than stainless steel. Silver epoxy comprises an epoxy that is laced with silver particles to make it electrically conductive. Silver epoxy may be used as an alternative to a solder and cures by exposure to heat.

According to preferred aspects of the disclosure, systems and methods described herein may provide a stylet having a smaller overall outer diameter and, in particular, a smaller tip outer diameter to allow for better compatibility with PICCs. These stylets may have structure along their main body that gives more rigidity to the stylet and in turn to an assembly of the stylet with a PICC. The increased rigidity may facilitate insertion and navigation of the catheter and stylet through a patient's vasculature. In addition, the stylet may have a floppy or flexible tip that minimize trauma to blood vessels as the stylet and catheter assembly passes through the blood vessels.

Referring to FIG. 1, an intravascular device 100 is depicted. The intravascular device 100 includes a connector assembly 110, a hub member 120, a guard 130, and a stylet 200. The connector assembly 110 may be configured to attach or plug into a port in a computer (not depicted). Alternatively, the connector assembly 110 may be configured to attach to one or more cords or wires that attach or plug into a computer. The computer may include a processor that is configured to receive and process a signal from one or more sensors disposed on the stylet 200, as explained in further detail below. The hub member 120 and the guard 130 may provide strain relief for the stylet 200. The hub member 120 may also be used by a physician or other user to manipulate movement of the stylet 200. For example, a user may grasp the hub member 120 and rotate or otherwise move it to produce a desired movement of the stylet 200. The hub member 120 and the stylet 200 may be attached to one another such that turning or movement of the hub member 120 may apply torque or impart rotation and movement to the stylet 200.

According to some aspects of the disclosure, the hub member 120 and the connector assembly 110 may be configured to allow relative movement between them so that movement of the hub member 120 does not cause movement of at least the portion of the connector assembly 110 that connects to a computer or additional wiring (e.g., a proximal portion of the connector assembly 110) so as to not interrupt the connectively provided by the connector assembly 110 to a computer. According to other aspects of the disclosure, the hub member 120 and the connector assembly 110 may rotate together, and another component proximal to the connector assembly 110 may ensure that connectivity with a computer is maintained.

The intravascular device 100 may have a length L1, and the exposed portion of the stylet 200 may have a length L2. The length L2 may be approximately half of the length L1 of the intravascular device 100. In an aspect, the length L1 may be 72 inches, and the length L2 may be 35 inches.

Referring now to FIG. 2a, a deconstructed view of the intravascular device 100 is depicted. The connector assembly 110 includes a proximal end for connecting to a computer or one or more cords or wires that connect to a computer. The connector assembly 110 also includes additional components 114 and 116 for receiving one or more electrical conductors or cables of the stylet 200. For example, one or more of components 114 and 116 of the connector assembly 110 may have a plurality of pin connectors for receiving a coaxial cable 216 and an electrical wire 214 of the stylet 200 (described below). In some aspects of the disclosure, the coaxial cable 216 and the electrical wire 214 of the stylet 200 may be soldered to one or more of the components 114 and 116 of the connector assembly 110. The coaxial cable 216 and the electrical wire 214 may receive signals from one or more sensors disposed on the stylet 200, as described in further detail below. The connector assembly 110 may also include one or more projections 112 for attaching the connector assembly 110 to the hub member 120. In an aspect, the projections 112 of the connector assembly 110 may latch into indentations 122 disposed on the inside of the hub member 120. The intravascular device 100 further includes a clamp 118 for holding the stylet 200 in place relative to other components of the intravascular device 100 (e.g., the hub member 120, the guard 130, the connector assembly 110). When the hub member 120 and the connector assembly 110 are assembled together, the clamp 118 may be disposed in a recess 124 within the hub member 120.

FIG. 2b shows an enlarged view of an area A depicted in FIG. 2a. As shown in FIG. 2b, two electrical conductors 214 and 216 may extend from a proximal end of the guard 130. The electrical conductor 216 may be a coaxial cable that connects to an ultrasound transducer 230 (described below) disposed on the stylet 200, and the electrical conductor 214 may be a conductive wire that connects to an ECG electrode 220 (described below) disposed on the stylet 200. The conductors 214 and 216 may receive signals from the ultrasound transducer 230 and the ECG electrode 220 and convey those signals to a computer or processor via the connector assembly 110. As depicted in FIG. 2b, one of the conductors (e.g., conductor 216) may have a length L4 that is longer than a length L3 of the other conductor (e.g., conductor 214). In alternative aspects of the disclosure, the conductors 214 and 216 may have lengths that are substantially the same, or the length L3 of the conductor 214 may be longer than the length L4 of the conductor 216.

Figure 3:
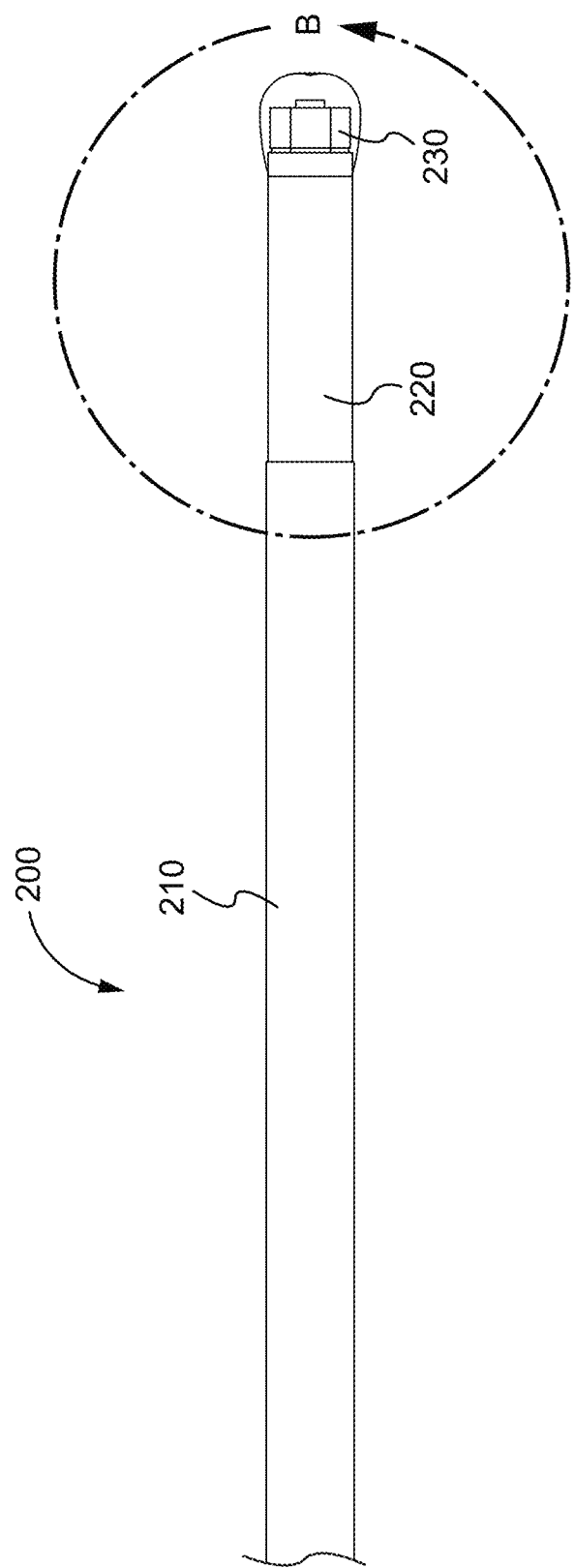
FIG. 3 is an enlarged view of a distal portion of a flexible tip stylet.

Referring now to FIG. 3, a distal portion of the stylet 200 is depicted. The stylet 200 includes an elongate member 210, an ECG ring electrode 220, and an ultrasound transducer or sensor 230. The elongate member 210 may comprise an elongated tube formed of a polymer, such as polyimide. The elongate member 210 may have a proximal end (not depicted) and a distal end. The ring electrode 220 may comprise a cylindrical marker band formed of a conductive material with low solution impedance, such as platinum iridium. The ring electrode 220 may provide an in vivo ECG signal of a patient. The ultrasound transducer 230 may be a non-imaging ultrasound transducer that provides in vivo non-image based ultrasound information of a patient's vasculature. In other aspects, the ultrasound transducer 230 may be replaced with another type of sensor or a plurality of different types of sensors that is mounted to the distal end of the stylet 200. For example, the ultrasound transducer 230 may be replaced with one or more of a pressure sensor, an optical sensor, a biosensor, or some other type of sensor for detecting and measuring a physiological parameter in a patient's vasculature. The ultrasound transducer 230 may provide Doppler ultrasound information that helps identify blood flow information in proximity to the ultrasound transducer 230. The ultrasound transducer 230 may comprise an ultrasound transmitter and an ultrasound receiver. The ultrasound transmitter may transmit an ultrasound signal into a patient's vascular system, and the ultrasound receive may receive a reflected ultrasound signal from the patient's vascular system. The reflected ultrasound signal may indicate a blood flow rate in the vicinity of the ultrasound transducer 230. In certain aspects, the ultrasound transducer 230 may have a cross-sectional shape that is hexagonal. In some aspects, the ultrasound transducer 230 may have an ultrasound transmitter that extends more distally than an ultrasound receiver. In other aspects, the ultrasound transducer 230 may have an ultrasound receiver that extends more distally than an ultrasound transmitter. As depicted in FIG. 3, the ring electrode 220 may be disposed at a distal end of the elongate member 210, and the ultrasound transducer 230 may be disposed at a distal end of the ring electrode 220.

According to aspects of the disclosure, systems and methods disclosed herein may determine a position of the distal end of the stylet 200 in a patient's vasculature based on specific blood flow and ECG information collected by the ring electrode 220 and the ultrasound transducer 230. Example methods of using ECG information and ultrasound information (indicative of blood flow rate) to determine a position of a catheter or stylet are described in U.S. Pat. No. 8,597,193, filed on Jun. 26, 2008, and U.S. Pat. No. 8,965,490, filed Mar. 14, 2013, incorporated herein by reference. In some aspects, the stylet 200 may be placed within an inner lumen of a catheter body (not depicted). The distal end of the stylet 200 may be aligned or positioned beyond a distal end or tip of the catheter body. And the stylet 200 may be used to guide the catheter through a patient's vasculature. For example, the stylet 200 may be positioned within a catheter, such as a PICC, and the catheter may be inserted, advanced, and positioned within a patient's vasculature based on readings and measurements (e.g., blood flow patterns, ECG signals) received from the stylet. The elongate member 210 of the stylet 200 may be formed of a lubricative material that facilitates insertion and placement of the stylet 200 within a catheter body.

Referring now to FIGS. 4 and 5, detailed views of the distal tip of the stylet 200 are shown. FIG. 4 depicts an enlarged view of a region B of the stylet 200, as marked in FIG. 3. And FIG. 5 depicts a cross-sectional view of a distal portion of the stylet 200. As shown in FIG. 5, the stylet 200 further includes an adaptor member 218 in the form of a cylindrical band. The elongate member 210 may cover or overlap a proximal portion of the adaptor member 218. The elongate member 210 may be attached to the proximal portion of the adaptor member 218 along this overlapping region. An adhesive, such as Loctite® 4014™ adhesive (a transparent, colorless, ethyl-based adhesive), may be used to attach the elongate member 210 to the proximal portion of the adaptor member 218. The attachment may form a fluid-tight seal between the elongate member 210 and the adaptor member 218. The distal end of the elongate member 210 may be adjacent to (e.g., butt up against) a proximal end of the ring electrode 220. The outer diameter of the distal end of the elongate member 210 and the outer diameter of the proximal end of the ring electrode 220 may be substantially the same or equal such that a smooth transition is created between the elongate member 210 and the ring electrode 220, thereby minimizing the risk of the tip snagging against vessel tissue.

The stylet 200 may have a distal portion that is more flexible than a proximal portion. According to aspects of the disclosure, a distal portion of the stylet may be more flexible because the stylet includes an electrical conductor (e.g., an electrical wire) that is more flexible at a distal portion than a proximal portion. For example, the stylet 200 includes a first electrical conductor 214. The electrical conductor 214 may comprise a conductive metal wire, such as a stainless steel wire. The electrical conductor 214 may be configured to convey an ECG signal from the ring electrode 220 to a computer or processor. As depicted in FIG. 5, the electrical conductor 214 may have a tapered distal segment, e.g., a distal segment with a tapered surface. The tapered distal segment may taper from a larger diameter to a smaller diameter in a direction toward the distal end of the electrical conductor 214. Due to the tapering, the electrical conductor 214 may be more flexible toward its distal end when compared to its proximal end. The tapered distal segment of the electrical conductor 214 may be disposed in the distal portion of the stylet; therefore, the distal portion of the stylet 200 may be more flexible due to the greater flexibility of the tapered distal segment of the electrical conductor 214.

The tapered distal segment of the electrical conductor 214 includes a distal portion that is attached to an inside surface of the adaptor member 218. According to some aspects of the disclosure, the electrical conductor 214 may be attached to the inside surface of the adaptor member 218 via soldering or welding. According to other aspects, the electrical conductor 214 may be attached to the inside surface of the adaptor member 218 using a conductive adhesive such as silver epoxy in addition to or in lieu of soldering/welding.

The adaptor member 218 includes a distal portion that is attached to an inside surface of the ring electrode 220. According to some aspects of the disclosure, the adaptor member 218 may be attached to the inside surface of the ring electrode 220 via soldering or welding. According to other aspects, the adaptor member 218 may be attached to the inside surface of the ring electrode 220 using a conductive adhesive such as silver epoxy in addition to or in lieu of soldering/welding. The attachment between the adaptor member 218 and the ring electrode 220 may form a fluid-tight seal between the two components. The adaptor member 218, through its attachments to the electrical conductor 214 and the ring electrode 220, connects the electrical conductor 214 to the ring electrode 220. Because the adaptor member 218 is attached to the elongate member 210, the electrical conductor 214, and the ring electrode 220, the adaptor member 218 provides a stable and secure connection between the electrical conductor 214 and the ring electrode 220.

The adaptor member 218 may be formed of stainless steel or another conductive material. The adaptor member 218 may have an outer diameter that is smaller than an outer diameter of the elongate member 210 and an outer diameter of the ring electrode 220. As depicted in FIG. 5, the proximal portion of the adaptor member 218 is disposed within the elongate member 210 and the distal portion of the adaptor member 218 is disposed within the ring electrode 220. According to certain aspects of the disclosure, equal portions of the adaptor member 218 may be disposed within the elongate member 210 and the ring electrode 220. In other aspects, a greater or smaller portion of the adaptor member 218 may be disposed within the elongate member 210 than the ring electrode 220. Due to the smaller diameter of the adaptor member 218, the maximum inner diameter of the stylet 200 decreases in the region with the adaptor member 218. The overall diameter of the stylet 200, however, does not need to increase to account for this smaller diameter region due to the tapering of the electrical conductor 214. Because the electrical conductor 214 also tapers to a smaller diameter in the region with the adaptor member 218, this tapering creates more space within the stylet 200 to allow for the passage of a second conductor (described below) or other interior stylet components.

According to some aspects of the disclosure, the adaptor member 218 may also be scalloped (e.g., a portion of the adaptor member 218 may be cutout) to provide for additional clearance for other components within the stylet 200 (e.g., the second conductor 216).

The stylet 200 further includes a second conductor 216 that attaches to the ultrasound transducer 230. The conductor 216 may comprise a coaxial cable. The conductor 216 may be configured to receive and convey signals from the ultrasound transducer 230 to a computer or processor. The conductors 214 and 216 may be disposed within the inner lumen of the elongate member 210. According to an aspect, the conductors 214 and 216 may extend along the full length of the elongate member 210. And, in particular, the conductor 214 may extend from the distal portion of the adaptor 218 beyond the proximal end of the elongate member 210.

As shown in FIG. 5, the ultrasound transducer 230 is encapsulated within a first encapsulating member 234. The first encapsulating member 234 may be formed of a transparent material, such as an epoxy or other type of polymer. The first encapsulating member 234 may enclose the ultrasound transducer 230, thereby shielding or sealing it off from outside elements. As shown in FIG. 4, the ultrasound transducer 230 and the first encapsulating member 234 are also encapsulated within a second encapsulating member 232. The second encapsulating member 232 may form a second enclosure around the ultrasound transducer 230. The second encapsulating member 232 may be formed from the same material as the first encapsulating member 234, or a different material. Both encapsulating members 232 and 234 may be formed of transparent material such that they can be used as one or more lenses for the ultrasound transducer 230. The first encapsulating member 234 may form an enclosure around the ultrasound transducer 230 and attach or adhere to a distal portion of the coaxial cable or second conductor 216. The first encapsulating member 234 may attach to the second conductor 216 along a region where the second conductor 216 bends towards a central axis of the stylet 200. As depicted in FIG. 5, the second conductor 216 may initially occupy a lower half of the stylet 200 when the second conductor 216 shares the interior space of the stylet 200 with the first conductor 214. But due to the more distal positioning of the ultrasound transducer 230, the second conductor 216 may extend beyond a distal end of the first conductor 214 in order to connect to the ultrasound transducer 230. The ultrasound transducer 230 may be centered at the tip of the stylet 200 to create a smoother transition between the ring electrode 220 and the ultrasound transducer 230 and to avoid a lateral offset between the ring electrode 220 and the ultrasound transducer 230. Thus, the second conductor 216 may bend toward the center of the stylet 200 in the region where it extends beyond the first conductor 214. The second conductor 216 may extend beyond the first conductor 214 by a distance L7. According to some aspects of the disclosure, this distance L7 may be approximately 0.02 inches.

The second encapsulating member 232 may form an enclosure around both the ultrasound transducer 230 and the first encapsulating member 234 and attach or adhere to an outside surface of the ring electrode 220. Thus, the second encapsulating member 232 may form a fluid-tight seal between the ultrasound transducer 230 and the ring electrode 220. The second encapsulating member 232 may extend a distance L5 along a longitudinal length of the ring electrode 220. The second encapsulating member 232 may adhere to the outer surface of the ring electrode 220 along the distance L5. The distance L5 may be less than or equal to 0.015 inches. The fluid-tight seal formed by the second encapsulating member 232, along with fluid-tight seal between the elongate member 210 and the adaptor 218 and the fluid-tight seal between the adaptor 218 and the ring electrode 220, effectively seals off the inside of the tip of the stylet 200 from outside fluids and other materials. The second encapsulating member 232 may also have a curved or generally smooth surface that is atraumatic.

The first encapsulating member 234 may have an outer diameter L8, and the second encapsulating member 232 may have an outer diameter L6. The outer diameter L6 may be approximately 0.02 inches, and the outer diameter L8 may be approximately 0.0185 inches. In an aspect of the disclosure, the outer diameter L6 of the second encapsulating member 232 is greater than the outer diameter of the elongate member 210 and an outer diameter of the ring electrode 220. Thus, the outer diameter L6 of the second encapsulating member 232 represents the largest lateral dimension of the stylet 200.

Referring now to FIGS. 6a and 6b, a distal portion of an electrical conductor 314 is depicted. The electrical conductor 314 is another example of a conductor that is configured to convey an ECG signal from an ECG electrode to a processor. The electrical conductor 314 may be formed of stainless steel or another type of electrically conductive material. Similar to the electrical conductor 214, the electrical conductor 314 may have a distal portion that gradually tapers from a larger diameter L9 to a smaller diameter L10. This gradual tapering from the larger diameter L9 to the smaller diameter L10 may occur over a longitudinal distance of 2 to 3 inches. According to an aspect of the disclosure, the larger diameter L9 may be approximately 0.007 inches, and the smaller diameter L10 may be approximately 60-70% of the larger diameter L9 (e.g., 0.0045 inches). The gradual taper may be formed by grinding the distal end of the electrical conductor 314. FIG. 6b shows a cross-sectional view of the electrical conductor 314 along the line C-C. As depicted in FIG. 6b, the electrical conductor 314 has a circular cross-sectional area.

Referring to FIGS. 7a and 7b, a distal portion of an electrical conductor 414 is depicted. The electrical conductor 414 is another example of a conductor that is configured to convey an ECG signal from an ECG electrode to a processor. The electrical conductor 414 may also be formed of stainless steel or another type of electrically conductive material. The electrical conductor 414 may be used in place of the electrical conductor 214 in the stylet 200. The electrical conductor 414 may have a sharp taper (e.g., quick or fast taper). As depicted in FIG. 7a, the electrical conductor 414 has a larger outer diameter L11 (e.g., 0.007 inches) that sharply tapers to a smaller outer diameter L12 (e.g., 0.0045 inches). The sharp taper may occur over a longitudinal distance of less than one inch. Thus, the electrical conductor 414 may have a small diameter portion that extends approximately 2 to 3 inches. The sharp taper may be formed by grinding the distal end of the electrical conductor 414. FIG. 7b shows a cross-sectional view of the electrical conductor 414 along the line D-D. As depicted in FIG. 7b, the electrical conductor 414 has a circular cross-sectional area.

Figures 8A, 8B:
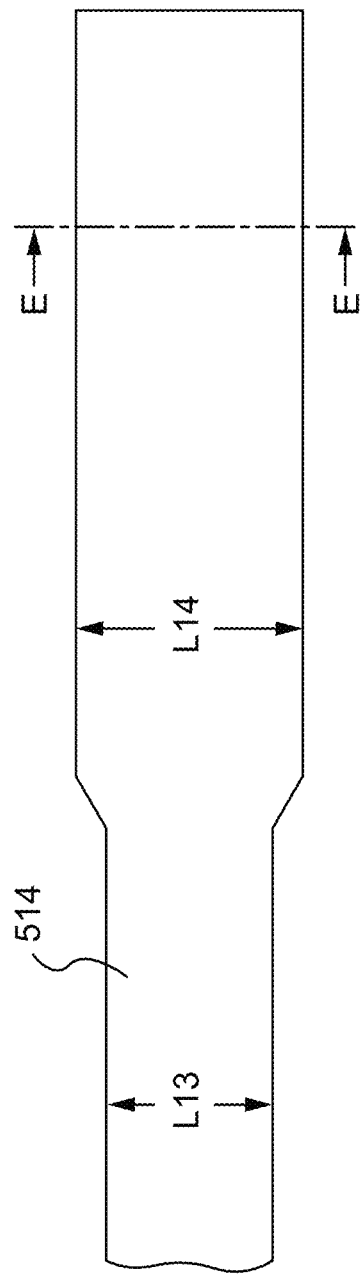
FIGS. 8a and 8b depict a third example of an electrical wire or conductor for conveying an ECG signal.

Referring to FIGS. 8a and 8b, a distal portion of an electrical conductor 514 is depicted. The electrical conductor 514 is another example of a conductor that is configured to convey an ECG signal from an ECG electrode to a processor. The electrical conductor 514 may also be formed of stainless steel or another type of electrically conductive material. The electrical conductor 514 may be used in place of the electrical conductor 214 in the stylet 200. The electrical conductor 514 may have a curved surface and a flattened surface, which may be formed by pressing the distal portion of the electrical conductor 514 into a die with a radius that matches a marker band or tube to which it attaches. For example, the electrical conductor 514 may be formed by pressing the distal end of the electrical conductor 514 into a die with a radius that matches that of an adaptor (e.g., the adaptor 218) that the electrical conductor 514 may attach to when it is assembled in a stylet (e.g., the stylet 200).

The electrical conductor 514 may have a circular portion with a diameter L13 (e.g., 0.007 inches) and a flattened portion with a flattened dimension L14 (as depicted in FIG. 8a) and a width L15 (as depicted in FIG. 8b). The flattened dimension L14 may be greater than the diameter L13. In an aspect, the flattened dimension L14 may be 40-50% greater than the diameter L13 (e.g., 0.01 inches). The width L15 may be smaller than the diameter L13. In an aspect, the width L15 may be approximately 60-70% of the diameter L13 (e.g., 0.0045 inches). FIG. 8b shows a cross-sectional view of the electrical conductor 314 along the line E-E. As depicted in FIG. 8b, the electrical conductor 514 can have a semi-oval or semi-circular cross-sectional area. This shape may allow for more flexibility when the electrical conductor 514 is flexed in a first direction along the width L15 of the electrical conductor 514 and less flexibility when the electrical conductor 514 is flexed in a second direction along the flattened dimension L14 of the electrical conductor 514.

Figure 9B:
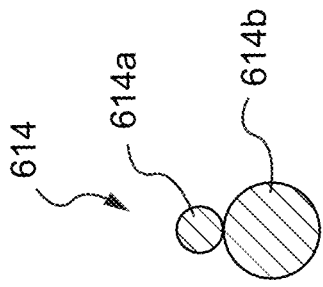
FIGS. 9a and 9b depict a fourth example of an electrical wire or conductor for conveying an ECG signal.
Figure 9A:
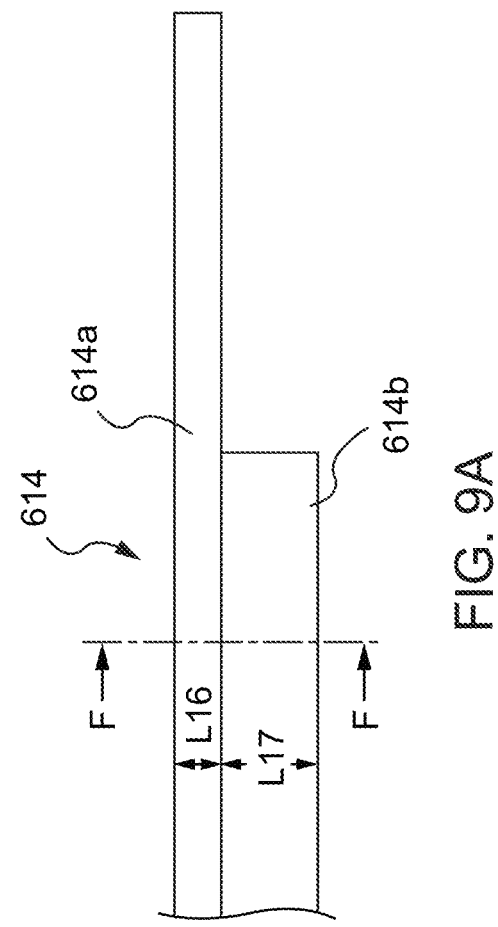

Referring to FIGS. 9a and 9b, a distal portion of an electrical conductor 614 is depicted. The electrical conductor 614 is another example of a conductor that is configured to convey an ECG signal from an ECG electrode to a processor. The electrical conductor 614 may also be formed of stainless steel or another type of electrically conductive material. The electrical conductor 614 may be used in place of the electrical conductor 214 in the stylet 200. The electrical conductor 614 may comprise a first wire 614a and a second wire 614b. The first wire 614a may have a smaller diameter L16, and the second wire 614b may have a larger diameter L17. According to an aspect of the disclosure, the diameter L17 of the second wire 614b may be approximately 0.007 inches, and the diameter L16 of the first wire 614a may be approximately 50-70% of the diameter L17 (e.g., 0.004 inches).

The first wire 614a may run a full length of a stylet, whereas the second wire 614b may run a portion of the full length of the stylet. As depicted in FIG. 9a, the first wire 614a may extend to a more distal point than the second wire 614b. In an aspect, the first wire 614a may extend an additional 2 to 3 inches beyond a distal end of the second wire 614b. The electrical conductor 614 may be more flexible in the region with the first wire 614b but without the second wire 614b. When assembled in a stylet (e.g., the stylet 200), a distal end of the first wire 614a may connect to a ring electrode (e.g., the ring electrode 220) or other type of ECG electrode, either directly or via an adaptor (e.g., the adaptor 218). FIG. 9b shows a cross-sectional view of the electrical conductor 614 along the line F-F. As depicted in FIG. 9b, the first wire 614a and the second wire 614b have circular cross-sectional areas.

Figure 10B:
FIGS. 10a and 10b depict a fifth example of an electrical wire or conductor for conveying an ECG signal.
Figure 10A:
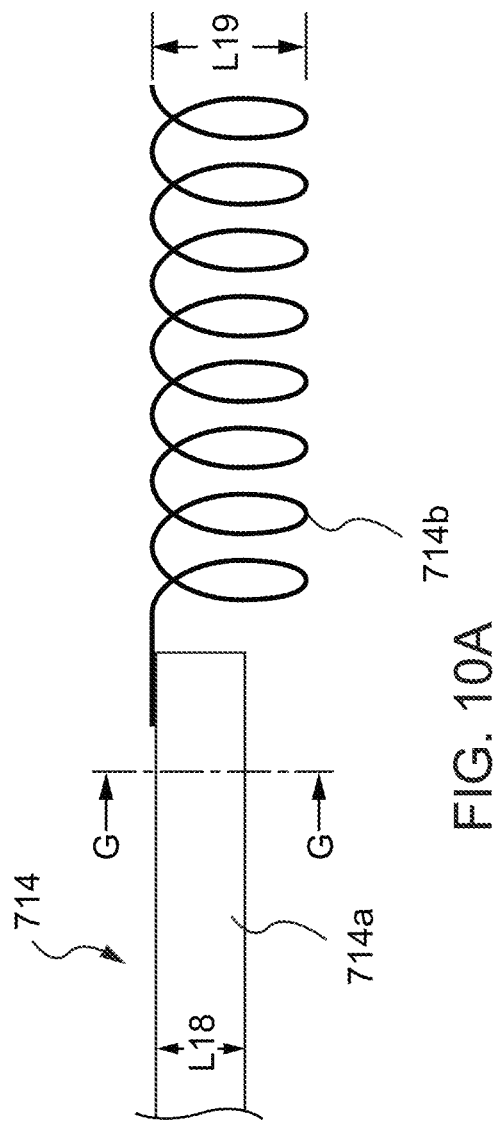

Referring to FIGS. 10a and 10b, a distal portion of an electrical conductor 714 is depicted. The electrical conductor 714 is another example of a conductor that is configured to convey an ECG signal from an ECG electrode to a processor. The electrical conductor 714 may also be formed of stainless steel or another type of electrically conductive material. The electrical conductor 714 may be used in place of the electrical conductor 214 in the stylet 200. The electrical conductor 714 may comprise a small-diameter coiled wire 714b that is welded onto a distal end of a stiffer wire 714a. The coiled wire 714b may extend 2 to 3 inches beyond the distal end of the stiffer wire 714a. The electrical conductor 714 may be more flexible in the region with the coiled wire 714b.

The stiffer wire 714a may have a diameter L18, and the coiled wire 714b may have a maximum outer diameter L19. The diameter L19 formed by the coiled wire 714b may be greater than the diameter L18 of the stiffer wire 714a. According to an aspect of the disclosure, the diameter L19 of the coiled wire 714b may be approximately 0.01 inches, and the diameter L18 of the stiffer wire 714a may be approximately 60-70% of the diameter L19 (e.g., 0.07 inches). When assembled in a stylet (e.g., the stylet 200), a distal end of the coiled wire 714b may connect to a ring electrode (e.g., the ring electrode 220) or other type of ECG electrode, either directly or via an adaptor (e.g., the adaptor 218). FIG. 10b shows a cross-sectional view of the electrical conductor 714 along the line G-G. As depicted in FIG. 10b, the stiffer wire 714a can have a circular cross-sectional area, and the coiled wire 714b can form circular-shaped coils.

Figure 11:
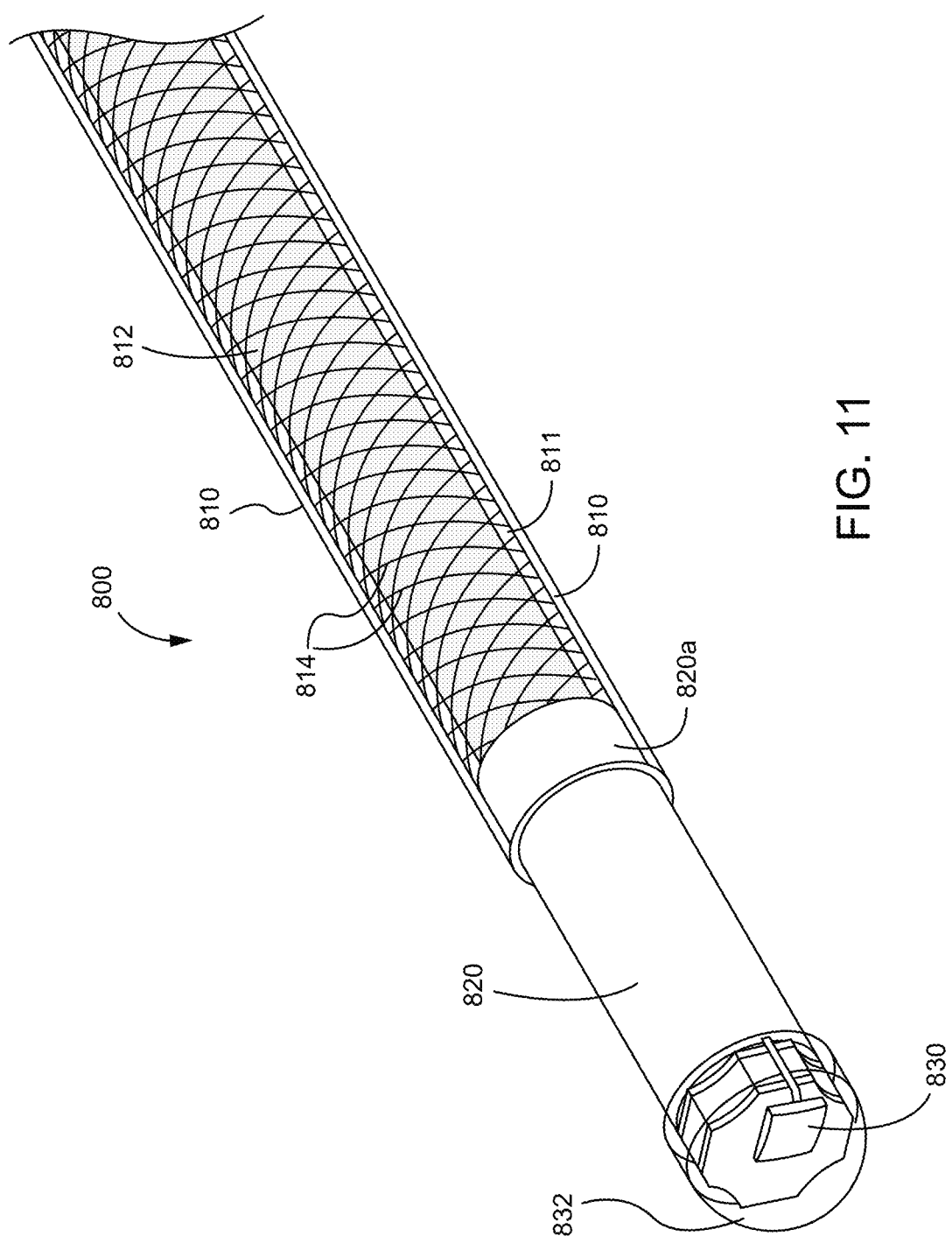
FIG. 11 is a perspective view of a distal portion of a flexible tip stylet having a braided electrical conductor.

Referring now to FIG. 11, a distal portion of a stylet 800 is depicted. Similar to the stylet 200, the stylet 800 may be a component an intravascular device, such as the intravascular device 100. Thus, a proximal portion of the stylet 800 may extend through a hub member (e.g., the hub member 120) and be connected to a connector assembly (e.g., the connector assembly 110, including connector components 114 and 116). The distal portion of the stylet 800, as depicted in FIG. 11, includes a sensor 830 and a marker band 820. The sensor 830 may be an ultrasound transducer, similar to the ultrasound transducer 230, or another type of sensor (e.g., a pressure sensor, a temperature sensor, an optical sensor, a biosensor). The sensor 830 may also comprise a plurality of different sensors, including an ultrasound transducer, a pressure sensor, an optical sensor, etc. The sensor 830 may be encapsulated within a transparent material 832, such as an epoxy or other polymeric material. The transparent material 832 may be rounded and smooth such that it forms an atraumatic tip. The transparent material 832 may also function as a lens that guides a beam or signal that is generated by the sensor 830. For example, if the sensor 830 was an ultrasound transducer, then the sensor 830 may transmit an ultrasound signal into a patient's vasculature. In such case, the transparent material 832 may function as a lens (or a plurality of lenses) that optimizes the ultrasound signal profile. Alternatively, if the sensor 830 was an optical sensor, then the sensor 830 may transmit a light beam into a patient's vasculature, and the transparent material 832 may also function as a lens (or a plurality of lenses) that optimizes the light signal profile.

The sensor 830 may be mounted on a distal end of the marker band 820. According to certain aspects of the disclosure, the transparent material 832 may enclose the sensor 830 and attach to an outer surface of a distal end of the marker band 820. As such, the transparent material 832 may form a fluid-tight seal between the marker band 820 and the sensor 830. The marker band 820 may comprise a cylindrical band, with a hollow inner lumen. The inner lumen of the marker band 820 may permit passage of a coaxial cable 812. The coaxial cable 812 may be an example of an electrical conductor. The coaxial cable 812 may extend through the inner lumen of the marker band 820 and attach to the sensor 830. The coaxial cable 812 may receive and convey signals from the sensor 830 to a computer via one or more additional connectors and wires. The coaxial cable 812 may extend along the entire length of the stylet 800.

The marker band 820 may function as an ECG electrode that is configured to measure an ECG signal from a patient's vasculature. The marker band 820 may be formed of a metallic material that has low solution impedance, such as platinum iridium. The marker band 820 may be attached to a braided conductor 814 that extends along a length of the stylet 800. The braided conductor 814 may comprise a plurality of electrically conductive wires (e.g., stainless steel wires) that are disposed between two tubular members 810 and 811. As depicted in FIG. 11, the braided conductor 814 is sandwiched between an outer tubular member 810 and an inner tubular member 811. The outer and inner tubular members 810 and 811 may be formed of a polymer such as polyimide. The braided conductor 814 may receive and convey ECG signals from the marker band 820 to a computer via one or more additional connectors and wires. The braided conductor 814 may extend along the entire length of the stylet 800.

In some aspects, the braided conductor 814 may have wound or braided wires that vary in pitch along a length of the stylet 800 in order to create regions that have variable stiffness. For example, the wires of the braided conductor 814 may have a larger pitch (e.g. separate coils that are more spaced apart) closer to a distal end of the stylet 800 to provide for more flexibility closer to the distal end of the stylet 800. In other aspects, the braided conductor 814 may have a lower wire count (e.g., a smaller number of wires) in some regions to vary the stiffness of the stylet. For example, the braided conductor 814 may have a lower wire count closer to a distal end of the stylet 800 to provide for more flexibility closer to the distal end of the stylet 800.

The marker band 820 may have a proximal portion 820a that is covered by one or both of the outer tubular member 810 and the inner tubular member 811. In other words, the outer tubular member 810 or the inner tubular member 811 may overlap a portion 820a of the marker band 820. This overlapping creates additional stability between the attachment of the marker band 820 and the braided conductor 814. Furthermore, the overlapping forms a fluid-tight seal between the tubular members 810 and 811 and the marker band 820. The tubular members 810 and 811 may be attached to the marker band 820 using an adhesive, such as Loctite® 4014™ adhesive.

According to aspects of the disclosure, systems and methods disclosed herein may determine a position of the distal end of the stylet 800 in a patient's vasculature based on specific blood flow and ECG information collected by the marker band 820 and the sensor 830. For example, specific blood flow patterns and ECG signals may be associated with particular locations within a patient's vasculature. In some aspects, the stylet 800 may be placed within an inner lumen of a catheter body (not depicted). The distal end of the stylet 800 may be aligned or positioned beyond a distal end or tip of the catheter body. And the stylet 800 may be used to guide the catheter through a patient's vasculature. For example, the stylet 800 may be positioned within a catheter, such as a PICC, and the catheter may be inserted, advanced, and positioned within a patient's vasculature based on readings and measurements (e.g., blood flow patterns, ECG signals) received from the stylet. The tubular member 810 of the stylet 800 may be formed of a lubricative material that facilitates insertion and placement of the stylet 800 within a catheter body.

Figure 12:
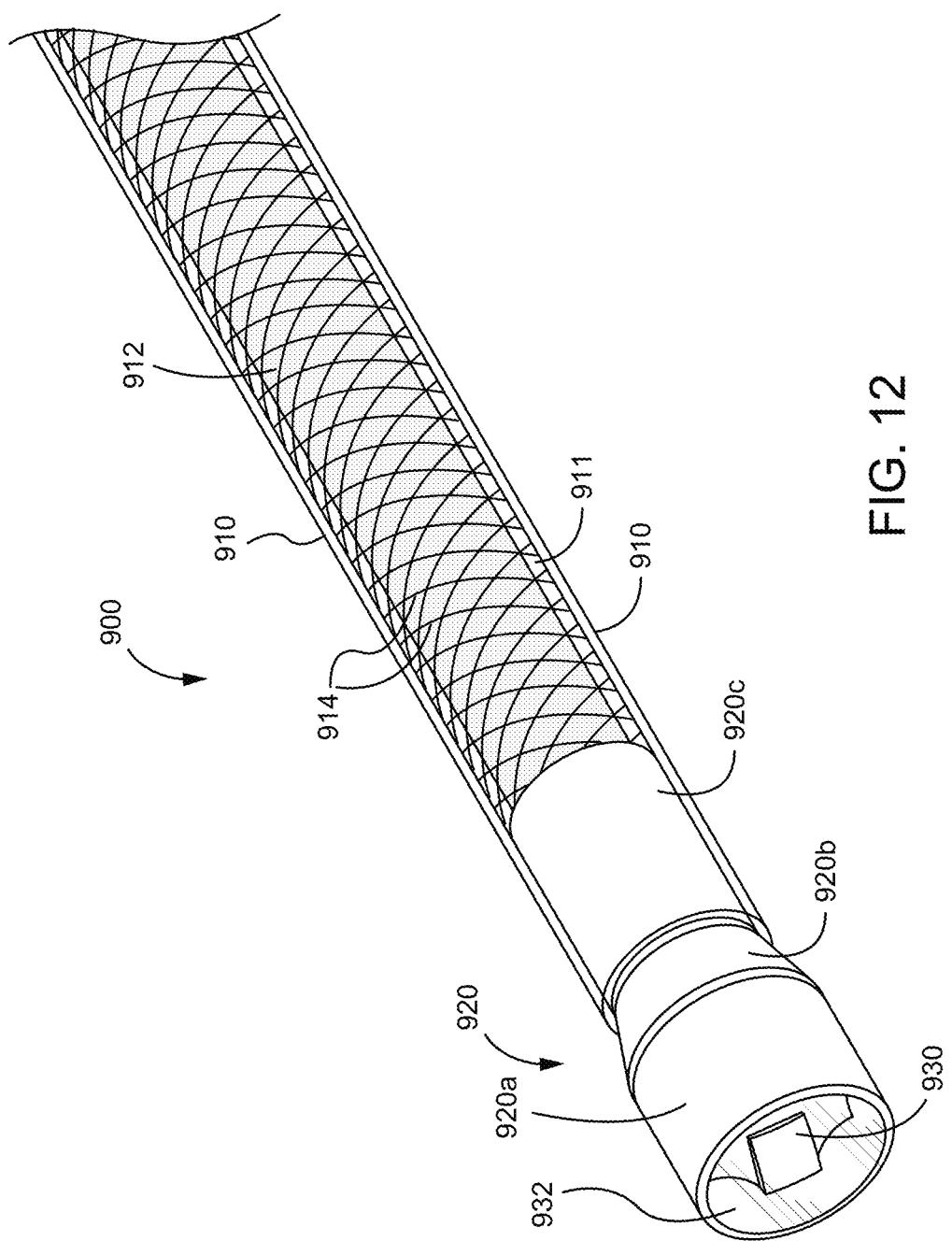
FIG. 12 is a perspective view of a distal portion of another flexible tip stylet having a braided electrical conductor.

Referring now to FIG. 12, a distal portion of a stylet 900 is depicted. Similar to the stylets 200 and 800, the stylet 900 may be a component an intravascular device, such as the intravascular device 100. Thus, a proximal portion of the stylet 900 may extend through a hub member (e.g., the hub member 120) and be connected to a connector assembly (e.g., the connector assembly 110, including connector components 114 and 116). The distal portion of the stylet 900 includes a sensor 930 and a marker band 920. The marker band 920 may be flared toward its distal end to allow the sensor 930 to be recessed within the marker band 920. In particular, as depicted in FIG. 12, the marker band 920 includes a first region 920a having a larger diameter within which the sensor 930 is recessed. The marker band 920 also includes a second region 920c with a smaller diameter that is covered by one or more tubular member 910 and 911. And the marker band 920 also includes a third region 920b that provides a transition between the first region 920a and the second region 920c.

Similar to the marker band 820, the marker band 920 may function as an ECG electrode that is configured to measure an ECG signal from a patient's vasculature. The marker band 920 may be formed of a metallic material that has low solution impedance, such as platinum iridium. The marker band 920 may be attached to a braided conductor 914 that extends along a length of the stylet 900. The braided conductor 914 may comprise a plurality of electrically conductive wires (e.g., stainless steel wires) that are disposed between the tubular members 910 and 911. As depicted in FIG. 12, the braided conductor 914 is sandwiched between the outer tubular member 910 and the inner tubular member 911. The outer and inner tubular members 910 and 911 may be formed of a polymer such as polyimide. The braided conductor 914 may receive and convey ECG signals from the marker band 920 to a computer via one or more additional connectors and wires. The braided conductor 914 may extend along the entire length of the stylet 900.

In some aspects, the braided conductor 914 may have wound or braided wires that vary in pitch along a length of the stylet 900 in order to create regions that have variable stiffness. For example, the wires of the braided conductor 914 may have a larger pitch closer to a distal end of the stylet 900 to provide for more flexibility closer to the distal end of the stylet 900. In other aspects, the braided conductor 914 may have a lower wire count (e.g., a smaller number of wires) in some regions to vary the stiffness of the stylet. For example, the braided conductor 914 may have a lower wire count closer to a distal end of the stylet 900 to provide for more flexibility closer to the distal end of the stylet 900.

As depicted in FIG. 12, the marker band 920 has a proximal region 920c that is covered by one or both of the outer tubular member 910 and the inner tubular member 911. In other words, the outer tubular member 910 or the inner tubular member 911 may overlap a region 920c of the marker band 920. This overlapping creates additional stability between the attachment of the marker band 920 and the braided conductor 914. Furthermore, the overlapping forms a fluid-tight seal between the tubular members 910 and 911 and the marker band 920. The tubular members 910 and 911 may be attached to the marker band 820 using an adhesive, such as Loctite® 4014™ adhesive.

The sensor 930 is recessed within the distal region 920a of the marker band 920. This recessing may provide added support for the sensor 930 as it navigates through a patient's vasculature. The sensor 930 may be an ultrasound transducer, similar to the ultrasound transducer 230, or another type of sensor (e.g., a pressure sensor, a temperature sensor, an optical sensor, a biosensor). The sensor 930 may also comprise a plurality of different sensors, including an ultrasound transducer, a pressure sensor, an optical sensor, etc. The distal region 920a of the marker band 920 may be filled with a transparent material 932 that encapsulates the sensor 930. The transparent material 932 may be an epoxy or other polymeric material. The transparent material 932 may form a fluid-tight seal between the marker band 920 and the sensor 930. The transparent material 932 may also function as a lens that guides a beam or signal that is generated by the sensor 930.

The marker band 920 may have a hollow inner lumen that permits passage of a coaxial cable 912. The coaxial cable 912 may be an example of an electrical conductor. The coaxial cable 912 may extend through the inner lumen of the marker band 920 and attach to the sensor 930. The coaxial cable 912 may receive and convey signals from the sensor 930 to a computer via one or more additional connectors and wires. The coaxial cable 912 may extend along the entire length of the stylet 900.

According to aspects of the disclosure, systems and methods disclosed herein may determine a position of the distal end of the stylet 900 in a patient's vasculature based on specific blood flow and ECG information collected by the marker band 920 and the sensor 930. For example, specific blood flow patterns and ECG signals may be associated with particular locations within a patient's vasculature. In some aspects, the stylet 900 may be placed within an inner lumen of a catheter body (not depicted). The distal end of the stylet 900 may be aligned or positioned beyond a distal end or tip of the catheter body. And the stylet 900 may be used to guide the catheter through a patient's vasculature. For example, the stylet 900 may be positioned within a catheter, such as a PICC, and the catheter may be inserted, advanced, and positioned within a patient's vasculature based on readings and measurements (e.g., blood flow patterns, ECG signals) received from the stylet. The tubular member 910 of the stylet 900 may be formed of a lubricative material that facilitates insertion and placement of the stylet 900 within a catheter body.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

We claim:

1. An intravascular device, comprising:
   a stylet comprising:
      an elongate member having a proximal end, a distal end, and an inner lumen extending between the proximal end and the distal end;
      a ring electrode extending from a distal-most end of the distal end of the elongate member;
      a sensor disposed at and extending directly from a distal end of the ring electrode and configured to detect and measure a physiological parameter in a patient's vasculature;
      a first electrical conductor disposed within the inner lumen of the elongate member and electrically connected to the ring electrode, the first electrical conductor configured to receive a first signal from the ring electrode and convey the first signal to a computing device; and
      a second electrical conductor disposed within the inner lumen of the elongate member and electrically connected to the sensor, the second electrical conductor configured to receive a second signal from the sensor and convey the second signal to the computing device;
   a hub having an inner lumen for receiving the stylet;
   a guard extending from a distal end of the hub, and having an inner lumen for receiving and stabilizing the stylet; and
   a connector assembly proximal to the stylet, configured for connecting the first and second electrical conductors of the stylet to a computing device;
   wherein the first electrical conductor includes a distal portion and a proximal portion, and the distal portion of the first electrical conductor of the stylet is more flexible than the proximal portion of the first electrical conductor of the stylet.

2. The intravascular device of claim 1, wherein the sensor comprises one or more selected from an ultrasound transducer, a pressure sensor, a temperature sensor, an optical sensor, a biosensor, or one or more combinations thereof.

3. The intravascular device of claim 1, wherein, the hub is configured to engage with the stylet wherein when in an engaged configuration, a rotation applied to the hub can cause a rotation to the stylet.

4. The intravascular device of claim 1, wherein the hub and the connector assembly are configured to allow relative movement between them so that movement of the hub does not cause movement of at least the portion of the connector assembly.

5. The intravascular device of claim 1, wherein the hub is configured to removably engage with the connector assembly so that the hub and connector assembly can rotate together, and wherein the connector assembly further comprises a stabilizing portion that rotates independent of the connector assembly such that the connection to the computing device is stable when the hub and connector assembly rotate.

6. The intravascular device of claim 1, wherein the connector assembly is configured to attach or plug into a port in a computer.

7. The intravascular device of claim 1, wherein the connector assembly is configured to attach to one or more cords or wires that attach to or plug into a computer.

8. The intravascular device of claim 1, wherein the intravascular device has a length L1 and the stylet has a length L2, wherein L2 is less than L1.

9. The intravascular device of claim 8, wherein is L1 is about two times L2.

10. The intravascular device of claim 1, wherein the second electrical conductor comprises a coaxial cable.

11. The intravascular device of claim 1, wherein the first electrical conductor comprises a conductive wire.

12. The intravascular device of claim 1, wherein the first electrical conductor is configured to convey an electrocardiogram signal from the ring electrode to the computing device.

13. The intravascular device of claim 1, further comprising a first encapsulating member forming a first enclosure around the sensor.

14. The intravascular device of claim 13, further comprising a second encapsulating member forming a second enclosure around the sensor and the first encapsulating member, wherein the second encapsulating member is attached to the ring electrode, and wherein the second encapsulating member forms a fluid-tight seal between the sensor and the ring electrode.

15. An intravascular stylet, comprising:
   an elongate member having a proximal end, a distal end, and an inner lumen extending between the proximal end and the distal end;
   a ring electrode disposed at the distal end of the elongate member;
   a sensor disposed at and extending directly from a distal end of the ring electrode, the sensor configured to detect and measure a physiological parameter in a patient's vasculature;
   a first electrical conductor configured to convey a first signal from the ring electrode to a computing device;

a second electrical conductor configured to convey a second signal from the sensor to the computing device, the first electrical conductor and the second electrical conductor being disposed within the inner lumen of the elongate member;

a first encapsulating member forming a first enclosure around the sensor; and a second encapsulating member forming a second enclosure around the sensor and the first encapsulating member, wherein the second encapsulating member is attached to the ring electrode, and wherein the second encapsulating member forms a fluid-tight seal between the sensor and the ring electrode.

16. The intravascular stylet of claim 15, wherein the first electrical conductor includes a distal portion and a proximal portion, and the distal portion of the first electrical conductor of the stylet is more flexible than the proximal portion of the first electrical conductor of the stylet.

17. An intravascular device comprising:
a stylet including:
an elongated tube having a proximal end, a distal end, and an inner lumen extending between the proximal end and the distal end;
an ECG electrode extending from a distal-most end of the distal end of the elongated tube;
an ultrasound transducer distal to the ECG electrode; and
an electrical conductor, the electrical conductor including:
a first electrical conductor at least partially within the inner lumen of the elongated tube and electrically connected to the ECG electrode, the first electrical conductor configured to receive a first signal from the ECG electrode and convey the first signal to a processor; and
a second electrical conductor at least partially within the inner lumen of the elongated tube and electrically connected to the ultrasound transducer, the second electrical conductor configured to receive a second signal from the ultrasound transducer and convey the second signal to the processor;
wherein a distal portion of the electrical conductor of the stylet is more flexible than a proximal portion of the electrical conductor of the stylet.

18. The intravascular device of claim 17, wherein the proximal portion the electrical conductor of the stylet includes a circular portion, and the distal portion of the electrical conductor of the stylet includes a flattened portion.

19. The intravascular device of claim 17, wherein the first electrical conductor has a first diameter, the second electrical conductor has a second diameter, and the second diameter is greater than the first diameter.

20. The intravascular device of claim 17, wherein the distal portion of the electrical conductor of the stylet comprises a coiled wire.

* * * * *